United States Patent
Pendergast et al.

(10) Patent No.: US 7,384,907 B2
(45) Date of Patent: Jun. 10, 2008

(54) METHOD OF TREATING INFECTION WITH ABL TYROSINE KINASE INHIBITORS

(75) Inventors: Ann Marie Pendergast, Durham, NC (US); Elizabeth A. Burton, Durham, NC (US)

(73) Assignee: Duke University, Durham, NC (US)

( * ) Notice: Subject to any disclaimer, the term of this patent is extended or adjusted under 35 U.S.C. 154(b) by 341 days.

(21) Appl. No.: 10/734,582

(22) Filed: Dec. 15, 2003

(65) Prior Publication Data

US 2005/0003377 A1 Jan. 6, 2005

Related U.S. Application Data

(60) Provisional application No. 60/507,088, filed on Oct. 1, 2003, provisional application No. 60/432,989, filed on Dec. 13, 2002.

(51) Int. Cl.
*A61K 31/00* (2006.01)
(52) U.S. Cl. .............................. 514/1; 435/15; 435/69.2
(58) Field of Classification Search ................... 435/15, 435/21, 69.2; 930/250
See application file for complete search history.

(56) References Cited

U.S. PATENT DOCUMENTS 5,521,184 A * 5/1996 Zimmermann ......... 514/252.11
5,969,101 A    10/1999 Pendergast et al.

OTHER PUBLICATIONS

Burton E. et al. Identification of a Novel Signaling Pathway for Uptake of Bacterial Pathogens. Molecular Biology of the Cell vol. 13(Suppl) p. 51a, abstract #286, 2002.*
Druker B. et al. Activity of a Specific Inhibitor . . . NEJM 344(14)1038-1043, Apr. 5, 2001.*
Burton et al, "bl tyrosine kinases are required for infection by *Shigella flexneri*" The EMBO Journal 22(20):5471-5479 (2003).
Burton et al, "Abl Kinases Regulate Actin Comet Tail Elongation via an N-WASP-Dependent Pathway", Molecular and Cellular Biology 25(20):8834-8843 (2005).
Burton et al, "The *Caenorhabditis elegans* ABL-1 Tyrosine Kinase Is Required for *Shigella flexneri* Pathogenesis", Applied and Environmental Microbiology 72(7):1-9 (2006).
Coyne and Bergelson, "Virus-Induced Abl and Ryn Kinase Signals Permit Coxsackievirus Entry through Epithelial Tight Junctions", Cell 124:119-131 (2006).
Reeves et al, "Disabling poxvirus pathogenesis by inhibition of Abl-family tyrosine kinases" Nature Medicine 11(7):731-739 (2005).
McFadden, "Gleevac casts a pox on poxviruses", Nature Medicine 11(7):711-712 (2005).
Burton et al, "Identification of a Novel Signaling Pathway Required for Update of Bacterial Pathogens", Molecular Biology of the Cell 13:51a, No. 286 (2002).
Druker et al, "Activity of a Specific Ingibitor of the BCR-ABL Tyrosine Kinase In the Blast Crisis Myeoloid Leukemia and Acite Lymphoblastic Leukenmia With the Philadelphia Crhomosome" N. Eng. J. Med. 344(14):1038-1042 (2001).
Chu and Yang, "c-Src protein kinase inhibitors block assembly and maturation of dengue virus", PNAS 104(9):3520-3525 (2007).
McFadden, "Gleevec casts a pox on poxviruses", Nature Medicine 11(7):711-712 (2005).
Reeves et al, "Disabling poxvirus pathogenesis by inhibition of Abl-family tyrosine kinases", Nature Medicine 11(7):731-739 (2005) & Supplementary Figs. 1-6 published online Jun. 26, 2005.
Reeves et al, "Corrigendum: Disabling poxvirus pathogenesis by inhibition of Abl-family tyrosine kinases", Nature Medicine 11(12):1361 2005.
Burton et al, "Abl tyrosine kinases are required for infection by *Shigella flexneri*", The EMBO Journal 22(20):5471-5479 (2003).
Burton et al, "Abl Kinases Regulate Actin Comet Tail Elongation via an N-WASP-Dependent Pathway", Molecular and Cellular Biology 25(20):8834-8843 (2005).
Burton et al, "The Caenorhabditis elegans ABL-1 Tyrosine Kinase Is Required for *Shigella flexneri* Pathogenesis", Applied and Environmental Microbiology 72(7):5043-5051 (2006).
Pendergast, "The Abl Family Kinases: Mechanisms of Regulation and Signaling", Advances in Cancer Research, pp. 51-100 (2002).

* cited by examiner

*Primary Examiner*—Ralph Gitomer
(74) *Attorney, Agent, or Firm*—Nixon & Vanderhye P.C.

(57) ABSTRACT

The present invention relates to a method of preventing or treating a pathogen infection comprising administering to a mammal in need thereof an effective amount of an inhibitor of Abl tyrosine kinase.

18 Claims, 9 Drawing Sheets

SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 1
agaagctttg caacaaacta ctgcttga                                              28

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
gcgctctaga ggaagagcca tatat                                                 25

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
atgttcgaac aacgcgtaaa ttct                                                  24

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
atgccgtatt ttttcaattt tttac                                                 25

METHOD OF TREATING INFECTION WITH ABL TYROSINE KINASE INHIBITORS

This application claims priority from U.S. Provisional Application No. 60/507,088, filed Oct. 1, 2003, and U.S. Provisional Application No. 60/432,989, filed Dec. 13, 2002, the entire contents of which are incorporated herein by reference.

TECHNICAL FIELD

The present invention relates, in general, to pathogens and, in particular, to a method of blocking pathogen infection and to a method of identifying agents suitable for use in such a method.

BACKGROUND

Multiple bacterial pathogens have evolved mechanisms that engage intracellular signaling pathways in the host cell to achieve successful infection (Zaharik et al, Int. J. Med. Microbiol. 291:593-603 (2002)). An example of such a pathogen is the Gram negative bacteria *Shigella flexneri*, the etiologic agent for the diarrheal disease shigellosis (Sansonetti, Am. J. Physiol. Gastrointest. Liver Physiol. 280: G319-323 (2001)). A key step in the pathogenesis of shigellosis is the ability of the bacteria to enter the normally non-phagocytic cells of the colonic mucosa. At the site of *Shigella* entry, the host actin cytoskeleton undergoes dramatic changes, including the formation of filopodia and lamellipodia, which are subsequently organized into long, actin-rich extensions that engulf the invading bacterium (Adam et al, J. Cell Biol. 129:367-381 (1995)). The changes in the actin cytoskeleton observed during *Shigella* infection are mediated by bacterial effectors that are part of a Type III Secretion System (TTSS) that is activated following contact between the bacterium and the host cells. The TTSS inserts a pore complex, comprised of *Shigella* proteins IpaB and IpaC, into the host cell plasma membrane that allows for delivery of other bacterial effector proteins into the host cell (Zaharik et al, Int. J. Med. Microbiol. 291:593-603 (2002), Blocker et al, J. Cell Biol. 147:683-693 (1999), Tran Van Nhieu et al, EMBO J. 16:2717-2729 (1997), Niebuhr et al, Mol. Microbiol. 38:8-19 (2000)). A key event during the initial phase of infection is the induction of actin polymerization at the site of *Shigella* contact with the host cell membrane, which results in massive cytoskeletal rearrangements, and the formation of actin foci at the site of the invading bacterium (Adam et al, J. Cell Biol. 129:367-381 (1995)). The insertion of *Shigella* IpaC into the membrane results in changes in the actin cytoskeleton, characteristic of the activation of the Rho family GTPases Cdc42 and Rac (Tran Van Nhieu et al, EMBO J. 18:3249-3262 (1999)). Both Cdc42 and Rac localize to the site of bacterial entry, and their activation has been shown to be required for efficient uptake of *Shigella* (Mounier et al, *J. Cell Sci.* 112:2069-2080 (1999), Shibata et al, *Curr. Biol.* 12:341-345 (2002)). The tyrosine kinase Src is also translocated to the site of the invading bacterium, and is thought to act as both a positive and negative regulator of the entry process. Src exerts its positive role by promoting the formation of actin foci, but it also acts negatively to down-regulate Rho (Dumenil et al, J. Cell Biol 143:1003-1012 (1998), Dumenil et al, J. Cell Sci. 113:71-80 (2000)). However, the role of tyrosine phosphorylation in the uptake of *Shigella flexneri* has not been fully explored, and the link between tyrosine kinases and Rho GTPase-dependent actin polymerization during this process has yet to be defined.

The Abl tyrosine kinase has been shown to regulate Rac-dependent cytoskeletal dynamics in mammalian cells, suggesting that Abl kinases may play a role in bacterial uptake (Plattner et al, Genes Dev. 13:2400-2411 (1999)). The mammalian Abl family of tyrosine kinases is comprised of Abl and Arg (Abl2), and has been implicated in the regulation of cell proliferation, survival, adhesion, and migration (Pendergast, Adv. Cancer Res. 85:51-1-(2002)). While the functions of the constitutively active chimeric oncogene Bcr-Abl have been well described, the cellular functions of Abl and Arg have remained elusive. Genetic studies have implicated Abl and Arg in the regulation of cytoskeletal dynamics. *Drosophila melanogaster* that lack Abl exhibit defects in growth cone motility, axon guidance, and epithelial cell polarity (Pendergast, Adv. Cancer Res. 85:51-1-(2002)). The defective growth cone phenotype is identical to that of *Drosophila* lacking profilin, a protein known to be involved in cytoskeletal dynamics (Wills et al, Neuron 22:291-299 (1999)). A similar phenotype is observed in flies expressing dominant negative Cdc42, or mutants of Trio, a Guanine Nucleotide Exchange Factor (GEF) for Rac and Rho (Wills et al, Neuron 22:291-299 (1999), Liebl et al, Neuron 26:107-118 (2000), Bateman et al, Neuron. 26:93-106 (2000)). Since Rho family GTPases have been shown to regulate the formation of F-actin structures such as filopodia and lamellipodia, these observations suggest that *Drosophila* Abl may regulate cytoskeletal re-organization and cell motility. Mice lacking Abl and Arg also exhibit cytoskeletal defects, resulting in delayed closure of the neural tube, and death before embryonic day 11 (Koleske et al, Neuron. 21:1259-1272 (1998)). Normal neuroepithelium display an ordered pattern of actin filaments at their apical surface, where Abl and Arg are normally located. In the Abl/Arg null mice, this apical actin latticework pattern is absent, and unorganized bundles of actin filaments are found at the basolateral surface of the cell (Koleske et al, Neuron. 21:1259-1272 (1998)). Moreover, it has been shown that Abl is required for formation of Rac-dependent lamellipodia in response to PDGF (Plattner et al, Genes Dev. 13:2400-2411 (1999)). These properties of the normal Abl family tyrosine kinases are consistent with the observed changes in the actin cytoskeleton of Bcr-Abl-expressing cells. Expression of Bcr-Abl induces the formation of filopodia and lamellipodia, and extension of pseudopods onto a fibronectin matrix (Salgia et al, J. Clin. Invest. 100:46-57 (1997)). These cytoskeletal effects were found to be a result of the increased tyrosine kinase activity of Bcr-Abl, and were reversed in the presence of Abl kinase inhibitors (Gaston et al, Exp. Hematol. 28:351 (2000)). These studies demonstrate that the Abl family kinases regulate cytoskeletal dynamics. Furthermore, Abl and Arg are unique among all known tyrosine kinases in that they contain a carboxy-terminal actin binding domain, and have been shown to have actin bundling activity (Pendergast, Adv. Cancer Res. 85:51-100 (2002)). Altogether, the Abl kinases are uniquely suited to link extracellular stimuli, such as infection by bacterial pathogens, to reorganization of the actin cytoskeleton.

The present invention results, at least in part, from studies, demonstrating a requirement for Abl and Arg in *Shigella flexneri* infection, and linking the requirement for Abl kinase activity to the Rho family GTPases Cdc42 and Rac during bacterial uptake.

SUMMARY OF THE INVENTION

The present invention relates, in general, to pathogens and, in particular, to a method of blocking pathogen infection and to a method of identifying agents suitable for use in such a method.

Objects and advantages of the present invention will be clear from the description that follows.

BRIEF DESCRIPTION OF THE DRAWINGS

(FIG. 2A) Mouse embryo fibroblasts from mice lacking both Abl and Arg were reconstituted with either vector alone (Null) or with Abl and Arg expression constructs (Abl/Arg). The expression of Abl and Arg was confirmed by Western blotting with anti-Abl 8E9, which recognizes the catalytic domain of both Abl and Arg. Anti-β-tubulin immunoblotting was used to demonstrate equal protein loading. (FIG. 2B) Null (grey bars) or Abl/Arg cells (black bars) were infected with *Shigella flexneri* strains ATCC® serotype 2a (ATCC) or 2457T, and bacterial uptake was measured by the gentamicin protection assay. Results shown correspond to three independent experiments, each performed in triplicate. (FIG. 2C) Null or Abl/Arg cells plated on coverslips were infected with *Shigella flexneri* 2457T, and incubated with gentamicin to eliminate extracellular bacteria. The percentage of infected cells was quantitated by immunofluorescence microscopy. (FIG. 2D) Null or Abl/Arg cells (both GFP-positive, due to stable expression of MIGR1 plasmids) plated on coverslips were infected with *Shigella* 2457T and incubated with gentamicin to eliminate extracellular bacteria. Cells were immunostained with anti-GFP (green) and anti-*Shigella* (red) antibodies, and visualized by immunofluorescence microscopy. Calibration bars=50 µm. (FIG. 2E) Null or Abl/Arg cells were infected with either invasive (black bars) or plasmid-cured, non-invasive (grey bars) variants of *Shigella flexneri* 2457T, and bacterial uptake was measured by the gentamicin protection assay.

(FIG. 3A) Mouse embryo fibroblasts lacking (Null, grey bar) or expressing Abl and Arg (Abl/Arg, black bars) were infected with *Shigella flexneri* ATCC® serotype 2a in the presence of 0-10 µM STI571, and bacterial uptake was measured by the gentamicin protection assay. The asterisks represent concentrations of STI571 at which the decrease in uptake is statistically significant (p value<0.05). (FIG. 3B) Mouse embryo fibroblasts either lacking (Null) or re-expressing Abl and Arg (Abl/Arg) and Hela cells were infected with *Shigella flexneri* 2457T in the absence (black bars) or presence (grey bars) of 10 µM STI571, and bacterial uptake was measured by the gentamicin protection assay. Results shown correspond to three independent experiments, each performed in triplicate, and are normalized with respect to the 0 µM STI571 treatment. As the uptake of *Shigella* by the Null cells was much lower than that observed in the Abl/Arg cells, fold uptake was normalized separately for the three indicated cell types by comparison of bacterial internalization in the absence and presence of 5T 1571 for each individual cell type, rather than across cell types.

(FIG. 4A) Abl and Arg were immunoprecipitated from lysates of NIH-3T3 cells that were either uninfected (−) or infected with *Shigella flexneri* 2457T for 0-30 minutes. The immunoprecipitates were used in an in vitro kinase assay, using GST-Crk as a substrate. (FIG. 4B) NIH-3T3 cells were infected with *Shigella flexneri* 2457T for 0-90 minutes. Anti-Crk immunoprecipitates were examined by immunoblotting with anti-phospho-Crk-Y221 or anti-Crk (upper panels). Total lysates were examined by immunoblotting with anti-phospho-Src-Y418 or anti-Src (lower panels).

(FIG. 5A) Cells lacking (Null) or re-expressing Abl and Arg (Abl/Arg) were infected with *Shigella flexneri* 2457T for noted times. Anti-Crk immunoprecipitates were examined by immunoblotting with anti-phospho-Crk-Y221 and anti-Crk (upper panels). Anti-cortactin immunoprecipates were examined by immunoblotting with anti-phosphotyrosine and anti-cortactin (lower panels). (FIG. 5B) Hela cells were serum-starved for three hours in the presence or absence of STI571, and infected for the indicated times with *Shigella flexneri* 2457T. Anti-Crk immunoprecipitates were examined by immunoblotting with anti-phospho-Crk-Y221 and anti-Crk (upper panel). Anti-cortactin immunoprecipates were examined by immunoblotting with anti-phosphotyrosine and anti-cortactin (lower panels). (FIG. 5C) MIGR1 vector, Crk-WT, and Crk-Y222F were introduced into NIH-3T3 cells. Crk expression was analyzed by immunoblotting with anti-Crk (upper panel). Anti-β-tubulin immunoblotting was used to assess equal protein loading (lower panel). (FIG. 5D) NIH-3T3 cells expressing MIGR1 vector, Crk-WT, or Crk-Y222F were infected with *Shigella flexneri* strains ATCC® serotype 2a (black bars) or 2457T (grey bars), and bacterial uptake was measured by the gentamicin protection assay. Results shown correspond to three independent experiments, each performed in triplicate.

(FIG. 6A) Cells lacking (Null) or re-expressing Abl and Arg (Abl/Arg) were infected with *Shigella flexneri* 2457T for noted times. Lysates were incubated with GST-PBD to precipitate GTP-bound Cdc42 and Rac, and the bound proteins were analyzed by immunoblotting with anti-Rac and anti-Cdc42 (upper panels). Cellular lysates were examined by immunoblotting with anti-Rac and anti-Cdc42 (lower panels). (FIG. 6B) The GST-PBD binding assays to assess Rac (upper panel) or Cdc42 (lower panel) activation in the Null and Abl/Arg cells were quantitated by densitometry. Results correspond to three independent experiments. (FIG. 6C) Activated forms of Cdc42 and Rac (Cdc42-V12 and Rac-V12) were introduced into cells lacking Abl and Arg. Expression of Abl and Arg was analyzed by Western blotting with anti-Abl 8E9 (upper panel). Expression of myc-tagged Cdc42-V12 and Rac-V12 was analyzed by immunoblotting with anti-myc (middle panel). Anti-β-tubulin immunoblotting was used to assess equal protein loading (lower panel). (FIG. 6D) Null, Abl/Arg, and Null cells expressing Cdc42-V12, and Rac-V12 were infected with *Shigella flexneri*, and bacterial uptake was analyzed by the gentamicin protection assay. Results represent three independent experiments, each performed in triplicate. (FIG. 6E) NIH-3T3 cells expressing MIGR1 vector, Crk-WT, or Crk-Y222F were infected with *Shigella flexneri* 2457T for 30 minutes, and analyzed for Cdc42 and Rac activities using the GST-PBD binding assay, as in FIG. 6A. (FIG. 6F) The GST-PBD binding assays to assess Cdc42 or Rac activities in cells expressing Crk-WT or Crk-Y222F were quantitated by densitometry. Results correspond to three independent experiments.

(FIG. 7A) Hela cells were transfected with EGFP vector, EGFP-Abl, EYFP-Arg, or EGFP-Crk, as noted. Cells were lysed, and analyzed for fusion protein expression by immunoblotting with anti-GFP (upper panels). Anti-β-tubulin immunoblotting was used to assess equal protein loading (lower panel). (FIG. 7B) Hela cells expressing EGFP vector, EGFP-Abl, EYFP-Arg, or EGFP-Crk were infected with Shigella flexneri for 30 minutes, and analyzed by immunofluorescence microscopy. Sites of bacterial entry were identified by staining the bacteria with DAPI and staining the actin foci with Rhodamine-phalloidin (red, left panels). Abl, Arg, and Crk localization was performed by staining with anti-GFP (green, middle panels). These images were merged to show co-localization of Abl, Arg, and Crk with the focus of actin at the site of bacterial entry (yellow, right panels). The sites of actin foci formation and co-localization with Abl, Arg, and Crk are noted by the arrowheads. Calibration bar (shown in the right panel only) =50 μm.

(FIG. 8A) Mouse embryo fibroblasts lacking (Null) or re-expressing Abl and Arg (Abl/Arg), or wild-type (WT) MEFs were lysed and analyzed for expression of Abl and Arg by immunoblotting with anti-Abl 8E9, which recognizes the catalytic domain of both Abl and Arg. Anti-β-tubulin immunoblottiing was used to demonstrate equal protein loading. (FIG. 8B) Cells lacking (Null) or re-expressing Abl and Arg (Abl/Arg), or wild-type MEFs were infected with Shigella flexneri 2457T, and bacterial uptake was measured by the gentamicin protection assay. Results shown correspond to three independent experiments, each performed in triplicate.

(FIG. 9A) A non-invasive variant of Shigella flexneri 2457T was isolated by plasmid curing and isolation on Congo Red agar plates, as described (Maurelli et al, Infect. Immun. 43:397-401 (1984)). DNA was isolated from both the invasive and the non-invasive bacteria, and analyzed by PCR, as described (Picking et al, Protein Expr. Purif. 8:40 1-408 (1996)). The IpaC gene was amplified to test for the presence of the virulence plasmid, the Fis gene was amplified to control for the presence of genomic DNA. Primers for IpaC (5' primer: AGAAGCTTTGCAACAAACTACTGCTTGA (SEQ ID NO:1); 3' primer: GCGCTCTAGAGGAAGAGCCATATAT (SEQ ID NO:2)) and Fis (5' primer: ATGTTCGAA-CAACGCGTAAATTCT (SEQ ID NO:3); 3' primer: ATGC-CGTATTTTTTCAATTTTTTAC (SEQ ID NO:4)) were designed based on their published sequences (Picking et al, Protein Expr. Purif. 8:401-408 (1996); Wei et al, Infec. Immun. 71:2775-2786 (2003)). The expected sizes of the IpaC and Fis PCR products are noted on the right. (FIG. 9B) The invasive and non-invasive variants of Shigella flexneri 2457T were analyzed for the ability to invade Hela cells using the gentamicin protection assay, as described (Menard et al, Meth. Enzymol. 236:493-509 (1994)). Results represent three independent expenments, each performed in triplicate.

DETAILED DESCRIPTION OF THE INVENTION

Figure 1:
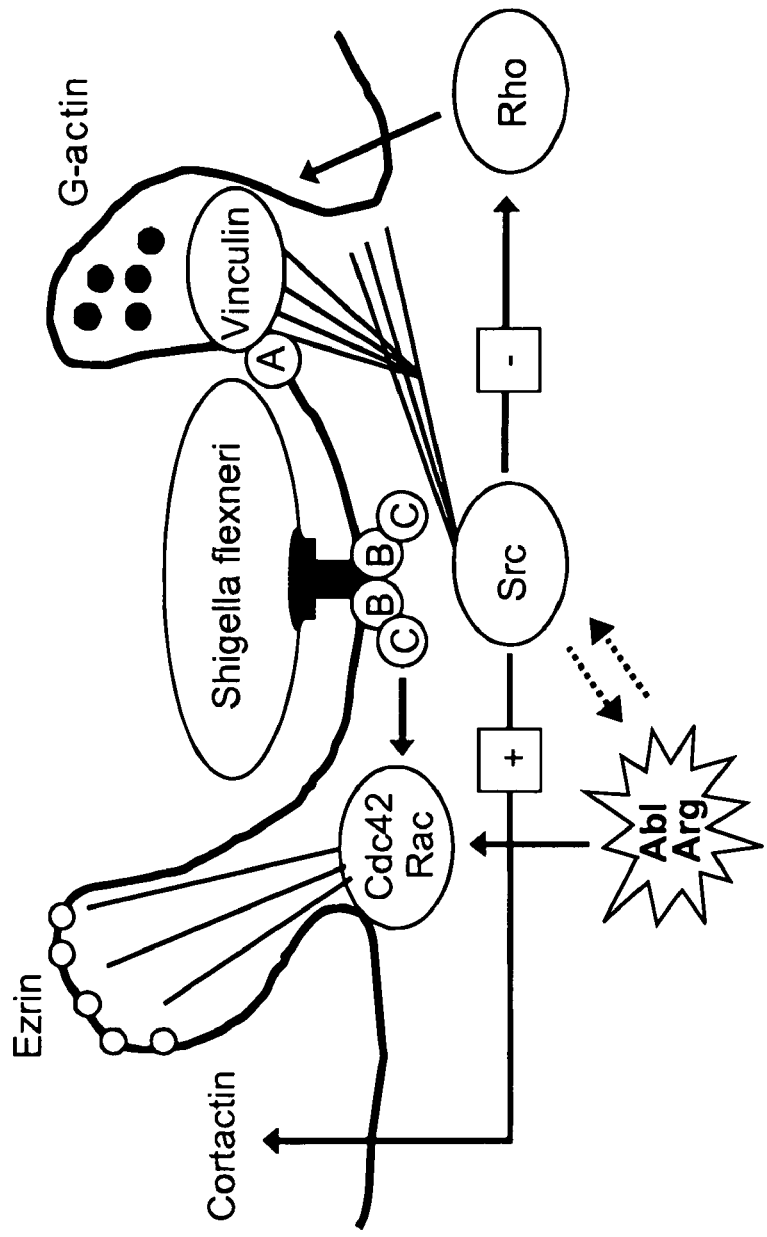
FIG. 1. Schemic of Abl and Arg function during bacterial uptake.

The present invention derives, at least in part, from a study demonstrating a novel role for the Abl tyrosine kinases in bacterial pathogenesis. The data presented in the Examples that follows demonstrate a requirement for the Abl family of tyrosine kinases in the cellular uptake of Shigella flexneri (see FIG. 1). Additionally, family members Abl and Arg are catalytically activated upon Shigella infection, accumulate at the site of bacterial entry, and are required for efficient bacterial uptake. The data demonstrate that the adaptor protein Crk is a target for Abl kinases during Shigella uptake. Moreover, a signaling pathway activated during Shigella entry is defined that links Abl kinase phosphorylation of Crk to activation of the Rho family GTPases Cdc42 and Rac.

The present invention relates, in one EMBOdiment, to a method of blocking pathogen infection. The method is applicable to any pathogen (e.g., bacterial or viral) that requries the Abl family of tyrosine kinases during infection. Examples of such bacterial pathogens include Shigella flexneri, Enteropathogenic E. coli and Salmonella. An example of a viral pathogen is vaccinia. The active agent used in this method is an inhibitor of Abl tyrosine kinase and is administered in an amount sufficient to effect the inhibition. It will be appreciated from a reading of this disclosure that the method can be used therapeutically or prophylactically. The present prevention/treatment method can be used to prevent/ treat infections in mammals, human and non-human (e.g., cats, dogs, cattle, pigs, horses, etc.).

In another EMBOdiment, the present invention relates to a method of screening test compounds for their suitability for use in the above described method. Such screens can be based on the ability of a test compound to inhibit Abl kinase activity. In vitro and cell-based assays can be used. In a typical in vitro assay, Abl and a substrate therefor (e.g., GST-Crk) is incubated in the presence and absence of test compound. A test compound that results in a decrease in substate phosphorylation is potentially useful in the present method of prevention/treatment.

Figure 4:
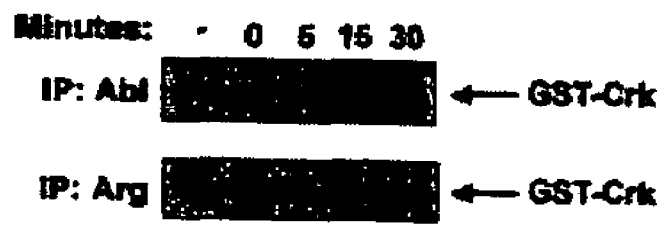
FIGS. 4A and 4B. Abl and Arg are catalytically activated during *Shigella* infection.
Figure 4:
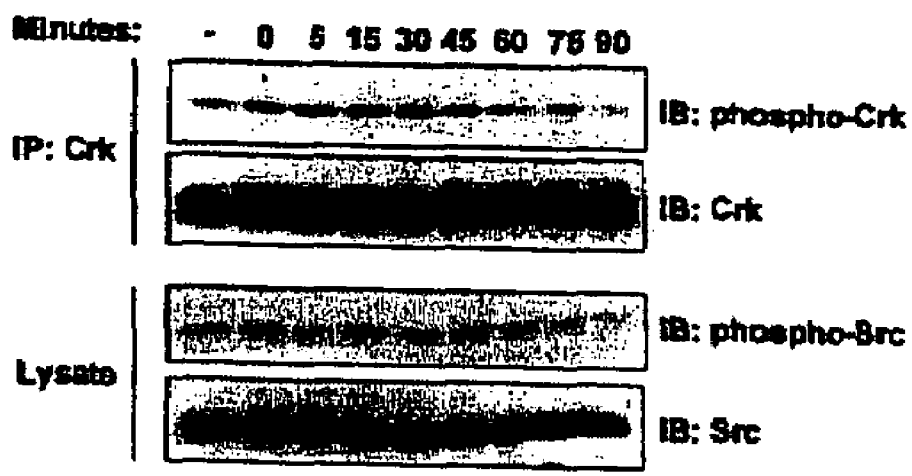

A similar approach can be used in cell-based assays. In this regard, attention is directed to the Example that follows and particularly to the portion thereof relating to FIG. 4. Compounds known to be suitable for use in the invention include STI571 and related compounds disclosed in U.S. Pat. No. 5,521,184.

It will be appreciated from a reading of this disclosure that inhibitors of upstream regulators of Abl kinase are also within the scope of the invention. That is, test compounds can be screened for their ability to inhibit upstream regulators, such as phospholipase-C-γ (PLCγ) and Src tyrosine kinases (see, for example Plattner et al, Nat. Cell. Biol. 5:309-319 (2003) and Plattner et al, Genes Dev. 13:2400-2411 (1999)), in addition to being screened for their ability to inhibit Abl kinase directly.

The invention further relates to novel compounds identifiable using the above screening method.

Compounds suitable for use in the present method can be formulated using standard techniques so as to yield compositions suitable for administration to mammals in need thereof. The compositions can include, for example, a pharmaceutically acceptable carrier, excipient or diluent. The choice of the carrier, excipient, diluent, or the like, can be selected based on whether the resulting composition is to be administered, for example, orally, intravenously, intraperitoneally, intradermally, intramuscularly, intranasally, buccally or topically. For oral administration, compositions can be present in dosage unit form, e.g., as tablets, pills, capsules, granules, drops, or the like, while for parenteral administration, the composition can take the form, for example, of a solution or suspension (advantageously sterile). Compositions suitable for topical administration can be present as, for example, liquids, creams gels or ointments. Compositions suitable for inhalative administration can be present in forms suitable for use as sprays. Agents of the invention can also be formulated as depot formulations, e.g., in dissolved form or in a transdermal device, optionally with the addition of agents promoting penetration of the skin when percutaneous administration is contemplated. Orally or percutaneously usable forms can provide for the delayed release of the agents of the invention. The amount of agent administered will depend, for example, on the nature of the agent, the status of the patient and the effect sought. Establishment of optimum dosing regimens is well within the skill level of one in the art.

Activation of the Abl tyrosine kinases can occur through a number of mechanisms (Pendergast, Adv. Cancer Res. 85:51-1-(2002)). Abl is normally held in an inactive conformation, whereby the SH3 domain interacts with a linker region between the SH2 and catalytic domains. Disruption of this conformation by mutations within the SH3 domain or the SH2-catalytic domain linker results in increased Abl catalytic activity. While not wishing to be bound by theory, it is possible that during infection (e.g., Shigella infection) a pathogen (e.g., bacterial pathogen) effector binds to Abl and Arg, disrupting the inactive conformation, leading to kinase activation. Additionally, tyrosine phosphorylation of Abl positively regulates its activity. Following stimulation of the PDGF receptor, Src phosphorylates Abl on tyrosine 245 and tyrosine 412 within the activation loop (Plattner et al, Genes Dev. 13:2400-2411 (1999), Brasher and Van Etten, J. Biol. Chem. 275:35631-35637 (2000)). Mutation of either tyrosine residue in Abl results in decreased kinase activity and reduced downstream signaling, indicating that tyrosine phosphorylation at one or both of these sites regulates catalytic activity (Brasher and Van Etten, J. Biol. Chem. 275:35631-35637 (2000), Furstoss et al, EMBO J. 21:514-524 (2002)). Activation of Src following infection may lead to tyrosine phosphorylation and activation of Abl and Arg. However, only a small pool of endogenous Abl protein is tyrosine phosphorylated and activated in response to growth factor stimulation or at the site of bacterial entry at the plasma membrane. Therefore, it is technically difficult to detect tyrosine phosphorylated Abl under these conditions (Pendergast, Adv. Cancer Res. 85:51-1-(2002)). In order to detect activated Abl proteins, two assays of greater sensitivity have been employed in the Example that follows, namely, immune-complex kinase assays and site-specific tyrosine phosphorylation of the Abl family substrate Crk.

Figure 5:
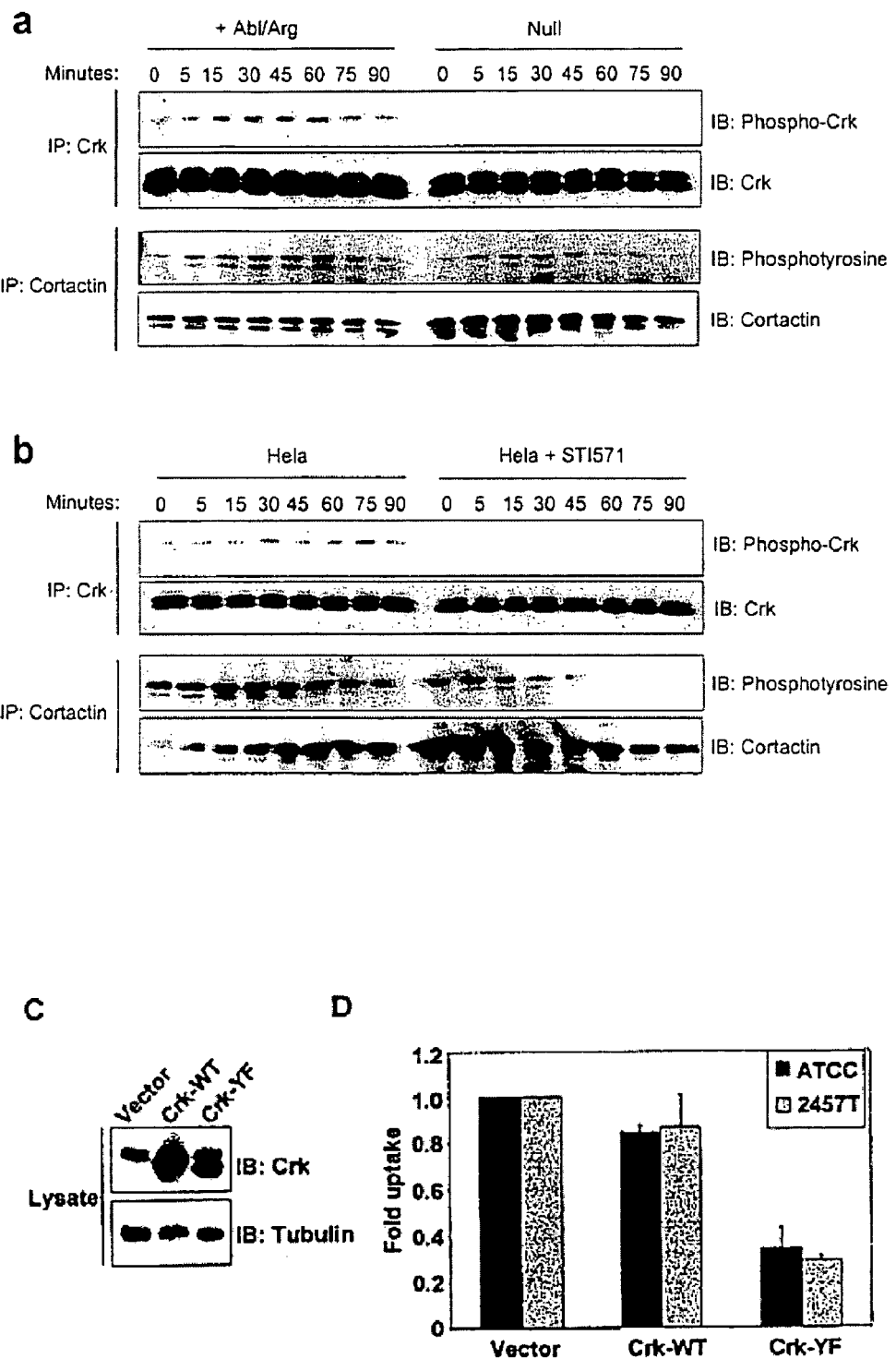
FIGS. 5A-5D. Crk and cortactin are phosphorylated by Abl kinases during *Shigella* entry and phosphorylation of Crk by the Abl kinases is required for *Shigella* internalization.

Two downstream targets of Abl and Arg kinase activity during Shigella infection have been identified, Crk and cortactin. Phosphorylation of Crk at tyrosine 221 by Abl in other processes, such as cell migration, has been well documented (Kain and Klemke, J. Biol. Chem. 276:16185-16192 (2001)). Crk has not previously been identified as a target of tyrosine kinases during infection. The fact that this site remains unphosphorylated in cells lacking the Abl family kinases indicates that Crk is a major target of Abl and Arg during infection (FIG. 5A). The tyrosine phosphorylation levels of cortactin are also decreased both in cells lacking Abl and Arg, and in cells treated with STI571 (FIG. 5). The induction of cortactin tyrosine phosphorylation during Shigella infection has been previously linked to Src kinase activity (Dehio et al, EMBO J. 14:2471-2482 (1995)). However, other kinases have also been shown to phosphorylate cortactin (Crostella et al, Oncogene 20:3735-3745 (2001), Kim and Wong, J. Biol. Chem. 273:23542-23548 (1998), Gallet et al, J. Biol. Chem. 274:23610-23616 (1999)). The study described in the Example that follows demonstrates that cortactin tyrosine phosphorylation is partly dependent upon Abl and Arg kinase activity. Abl kinases may phosphorylate cortactin directly, or mediate the activation of other endogenous tyrosine kinases that phosphorylate cortactin. Phosphorylation of cortactin is thought to disrupt the interaction between cortactin and F-actin, allowing for cytoskeletal rearrangements to proceed (Huang et al, J. Biol. Chem. 272:13911-13915 (1997)).

Abl kinases have been shown to regulate cytoskeletal rearrangements characteristic of Rac activation (Plattner et al, Genes Dev. 13:2400-2411 (1999), Pendergast, Adv. Cancer Res. 85:51-1-(2002)). Cdc42 and Rac can rescue the ability of cells lacking Abl and Arg to engulf Shigella flexneri. This observation indicates that Abl and Arg are upstream effectors in the signaling pathway regulating the activation of the Rho family GTPases. Indeed, the requirement for Abl and Arg during Shigella entry is similar to that of Rac and Cdc42. Expression of dominant negative forms of Rac and Cdc42 reduced the levels of Shigella internalization by 68-74% (Mounier et al, J. Cell Sci. 112:2069-2080 (1999)). Similarly, fibroblasts derived from Cdc42 knockout mice exhibit a 68-85% reduction in Shigella entry, compared to wild-type fibroblasts (Shibata et al, Curr. Biol. 12:341-345 (2002)). Abl/Arg-null fibroblasts exhibit a 79% to 93% decrease in Shigella infection, depending on the strain employed.

The Shigella effector IpaC has been shown to induce cytoskeletal rearrangements characteristic of Rho GTPase activation, however, IpaC does not itself exhibit GEF activity (Tran Van Nhieu, EMBO J. 18:3249-3262 (1999)). Abl and Arg may function to mediate this activation, by recruiting and/or activating a host cell GEF protein to the site of bacterial entry. Alternatively, Abl kinases may regulate Cdc42 and Rac indirectly via adapter proteins. Indeed, the Crk adapter has been shown to mediate activation of Rac, indicating that phosphorylation of Crk by Abl and Arg contributes to the activation of the Rho family GTPases during Shigella infection (Abassi and Vuori, EMBO J. 21:4571-4582 (2002)).

Certain aspects of the invention can be described in greater detail in the non-limiting Example that follows (see also Burton et al, The EMBO J. 22:5471 (2003) which is incorporated herein by reference, as are the references cited therein).

EXAMPLE

Experimental Details

Bacterial Strains and Infections

Figure 9:
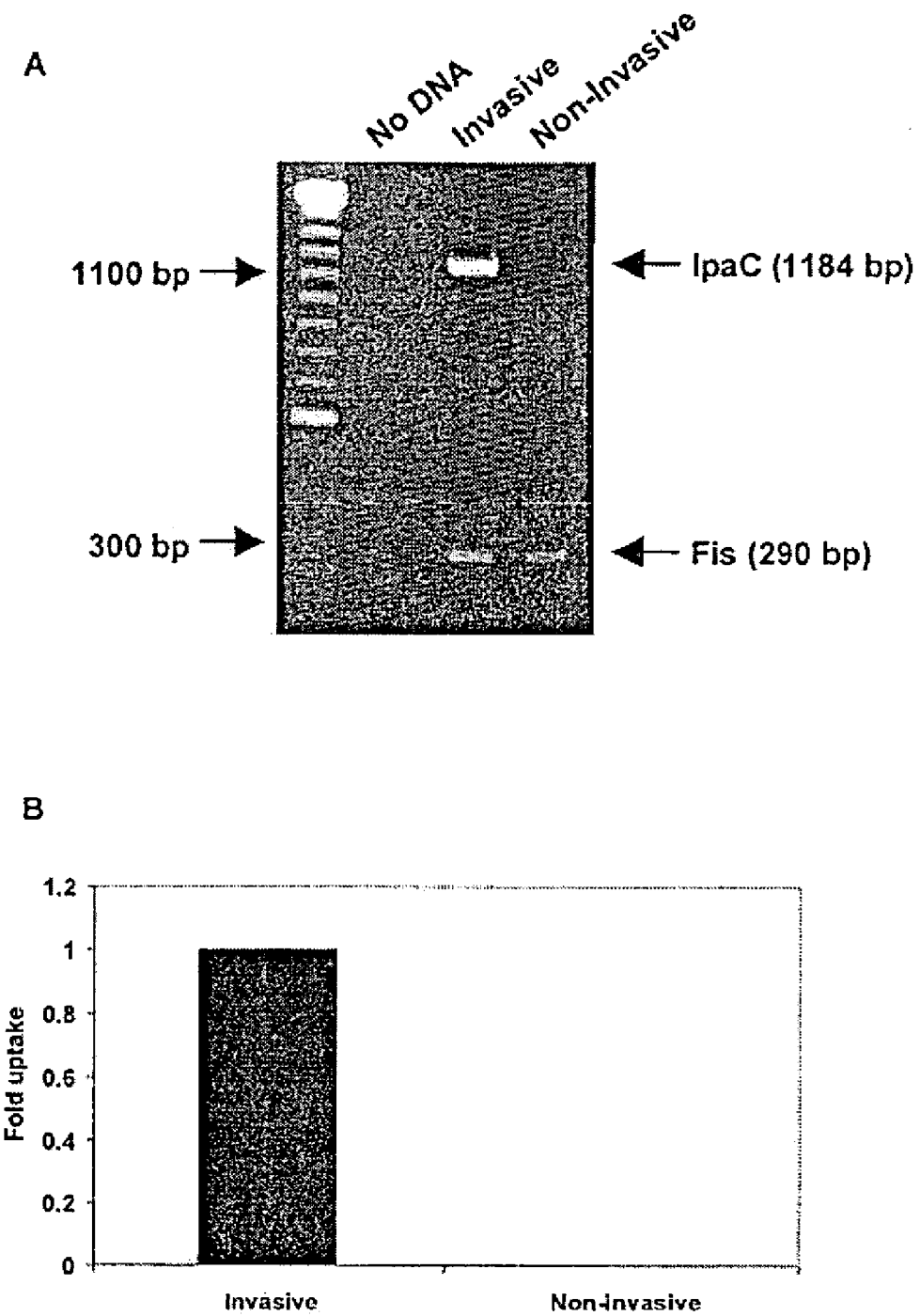
FIGS. 9A and 9B. Characterization of a non-invasive variant of Shigella flexneri 2457T.

The *Shigella flexneri* serotype 2a strain was obtained from the American Type Culture Collection. The *Shigella flexneri* 2457T strain was a gift from M. Goldberg (Harvard University). The non-invasive strain was created by plasmid curing the 2457T strain at 4° C. for three months, isolating white colonies on Congo Red agar plates, and analyzing the strain for Hela cell infectivity and presence of the virulence plasmid (FIG. 9). All strains were grown on Tryptic Soy Broth (TSB) agar plates and liquid cultures. For infection, overnight cultures of *S. flexneri* were grown in TSB, diluted 1:100, and grown to mid-logarithmic phase ($OD_{600}$=0.3).

Antibodies and Chemical Reagents

Anti-Arg antiserum was generated by injection of rabbits with a peptide comprised of a sequence unique to the Arg C-terminus (DKDRPRRVKPK). The following antibodies were obtained from commercial sources: anti-Abl 8E9 (BD Pharmingen), anti-Abl K12, anti-GFP, anti-myc 9E10, anti-Src, Horseradish peroxidase-linked goat anti-mouse IgG (Santa Cruz Biotechnology), anti-Cdc42, anti-Crk, anti-Rac (BD Transduction Laboratories), anti-*Shigella* (Maine Biotechnology Services), anti-phospho-Crk Y221 (Cell Signaling Technology), anti-cortactin, anti-phosphotyrosine (Upstate Biotechnology), anti-phospho-Src Y418 (Biosource), anti-β-tubulin (Sigma). Protein A-Sepharose, Protein G-Sepharose, Horseradish Peroxidase-linked Protein A, and the ECL Western Blotting Reagents were obtained from Amersham Biosciences. Rhodamine-phalloidin, DAPI, and Cy2- and Cy3-conjugated secondary antibodies were obtained from Molecular Probes. STI571 was a gift from B. Druker (Oregon Health Sciences University).

DNA Constructs

The pCan-Cdc42-V12 and pExv-Rac-V12 constructs were provided by A. Abo (Onyx Pharmaceuticals). The Cdc42 and Rac coding sequences were subcloned into the bicistronic retroviral vector MIGRL (Pear et al, Blood 92:3780-3792 (1998)). The MIGR1-c-Abl construct was previously described (Plattner et al, Genes Dev. 13:2400-2411 (1999)). The PK1-Arg expression construct was previously described (Plattner et al, Nat. Cell Biol. 5:309-319 (2003)). The chicken Crk constructs were a gift of R. Tsien (University of California, San Diego). The Crk coding sequences were amplified by PCR, and subcloned into MIGR1 and PEGFP (Clontech). The GST-PBD construct was provided by K. Burridge (University of North Carolina). The EGFP-Abl construct was provided by J.V. Small (Austrian Academy of Sciences). The EYFP-Arg construct (Wang et al, Proc. Natl. Acad. Sci. USA 98:14865-14870 (2001)) was provided by A. Koleske (Yale University).

Cell Culture

Mouse embryo fibroblasts (MEFs) from mice doubly null for Abl and Arg were provided by A. Koleske (Yale University), and were maintained in Dulbecco's Modified Eagle Medium (DMEM) supplemented with 10% fetal bovine serum (FBS) (Koleske et al, Neuron 21:1259-1272 (1998)). PK1-Arg was introduced into the MEFs by transfection and selection of a puromycin-resistant population. MIGR1 vector and MIGR1-c-Abl were introduced into null or Arg-expressing MEFs by retroviral infection, as described (Plattner et al, Nat. Cell Biol. 5:309-319 (2003)). MIGR1-Cdc42-V12 and MIGR1-Rac-V12 were introduced into the MEFs by retroviral infection, and GFP-positive cells were selected, as described (Plattner et al, Genes Dev. 13:2400-2411 (1999)). Hela cells were obtained from the Cell Culture Facility at the Duke Comprehensive Cancer Center, and were maintained in DMEM supplemented with 10% FBS. NIH-3T3 cells were provided by C. Der (University of North Carolina), and were maintained in DMEM supplemented by 10% calf serum (Hyclone). MIGR1-Crk constructs were introduced into NIH-3T3 cells by retroviral infection, as described (Plattner et al, Genes Dev. 13:2400-2411 (1999)). Hela cells were transfected using Lipofectamine (Invitrogen) according to the manufacturer's instructions.

Invasion Assays

The gentamicin protection assay was performed as described (Elsinghorst, Methods Enzymol. 236:405-420 (1994)). Briefly, mid-logarithmic phase bacteria were pelleted, and resuspended in DMEM containing 10% FBS and 50 mM Hepes, pH 7.3. The bacteria were overlayed onto a cell monolayer at a multiplicity of infection of 50, and the infection was initiated by centrifuging the plates at 700×g for 10 minutes. The plates were transferred to a 37° C. incubator for a 30-120 minute invasion incubation. The cell monolayers were washed, and media containing 50 μg/ml gentamicin was added for 2 hours. The cells were lysed with 1% Triton X-100, and diluted lysates were plated on TSB agar plates. The results presented are compiled from three independent experiments, each performed in triplicate. *Shigella* uptake was measured by dividing the number of internalized bacteria by the number of input bacteria (cfu/input). The fold uptake is a normalization of this calculation for each cell type or experimental condition. Analysis of invasion by immunofluorescence microscopy was performed as described (Shibata et al, Curr. Biol. 12:341-345 (2002)).

Immunoprecipitation and in Vitro Kinase Assays

Mid-logarithmic phase bacteria were resuspended in serum-free DMEM containing 50 mM Hepes, pH 7.3 and overlayed onto a cell monolayer. The plates were incubated at room temperature for ten minutes, and transferred to a 37° C. incubator for noted times. The 0 timepoint represents cells that were incubated with bacteria at room temperature for ten minutes, but not transferred to 37° C. The cells were washed with cold PBS, and lysed as for the in vitro kinase assay (Plattner et al, Genes Dev. 13:2400-2411 (1999)). Lysates were incubated with noted antibodies, and immunoprecipitated with Protein A- or Protein G-Sepharose. To infect cells for the in vitro kinase assay, bacteria were resuspended as above, overlayed onto a cell monolayer, and centrifuged at 700×g for 10 minutes. The plates were transferred to a 37° C. incubator for the noted times, and processed for use in the in vitro kinase assay, as described (Plattner et al, Genes Dev. 13:2400-2411 (1999)).

Cdc42 and Rac Activation Assays

The GST-PBD binding assay to assess endogenous Cdc42 and Rac activation was essentially performed as described (Bagrodia et al, J. Biol. Chem. 273:23633-23636 (1998)). In brief, the cells were infected with *Shigella flexneri* 2457T for 0-30 minutes as described above, washed with cold HBS, and lysed in a modified RIPA buffer (1% NP-40, 500 mM NaCl, 0.5% DOC, 0.1% SDS, 50 mM Tris, pH 8.0, 10 mM $MgCl_2$) containing protease and phosphatase inhibitors. Equal amounts of lysate were incubated with 20 μg GST-PBD for 30 minutes, and the beads were washed 3-5 times with HBS wash buffer (1% NP-40, 120 mM NaCl, 20 mM Hepes, 10 mM $MgCl_2$). The samples were separated by SDS-PAGE, transferred to nitrocellulose, and immunoblotted with either anti-Rac or anti-Cdc42. Cell lysates were examined by immunoblotting to demonstrate equal levels of total Rac and Cdc42 for each sample. Rac and Cdc42 activities were analyzed using densitometry and quantitated using ImageQuant software.

Immunofluorescence Microscopy

Cells plated on coverslips were infected with *Shigella flexneri* 2457T as described, washed with ice-cold PBS, and fixed in 4% paraformaldehyde. Cells were lysed in 0.5% Triton X-100 in 4% paraformaldehyde, washed with PBS, and incubated in block (2% BSA in PBS). Antibodies were diluted in block as follows: anti-GFP (1:100), anti-*Shigella* (1:20,000), Rhodamine-phalloidin (1:1000), DAPI (1:100,000), Cy2-anti-mouse secondary (1:100), Cy3-anti-rabbit secondary (1:2000). Samples were viewed at 63X magnification on a Zeiss Axioskop microscope, and analyzed using Metamorph software (Universal Imaging).

Results

Abl Family Kinases are Required for Uptake of *Shigella flexneri*

Figure 2:
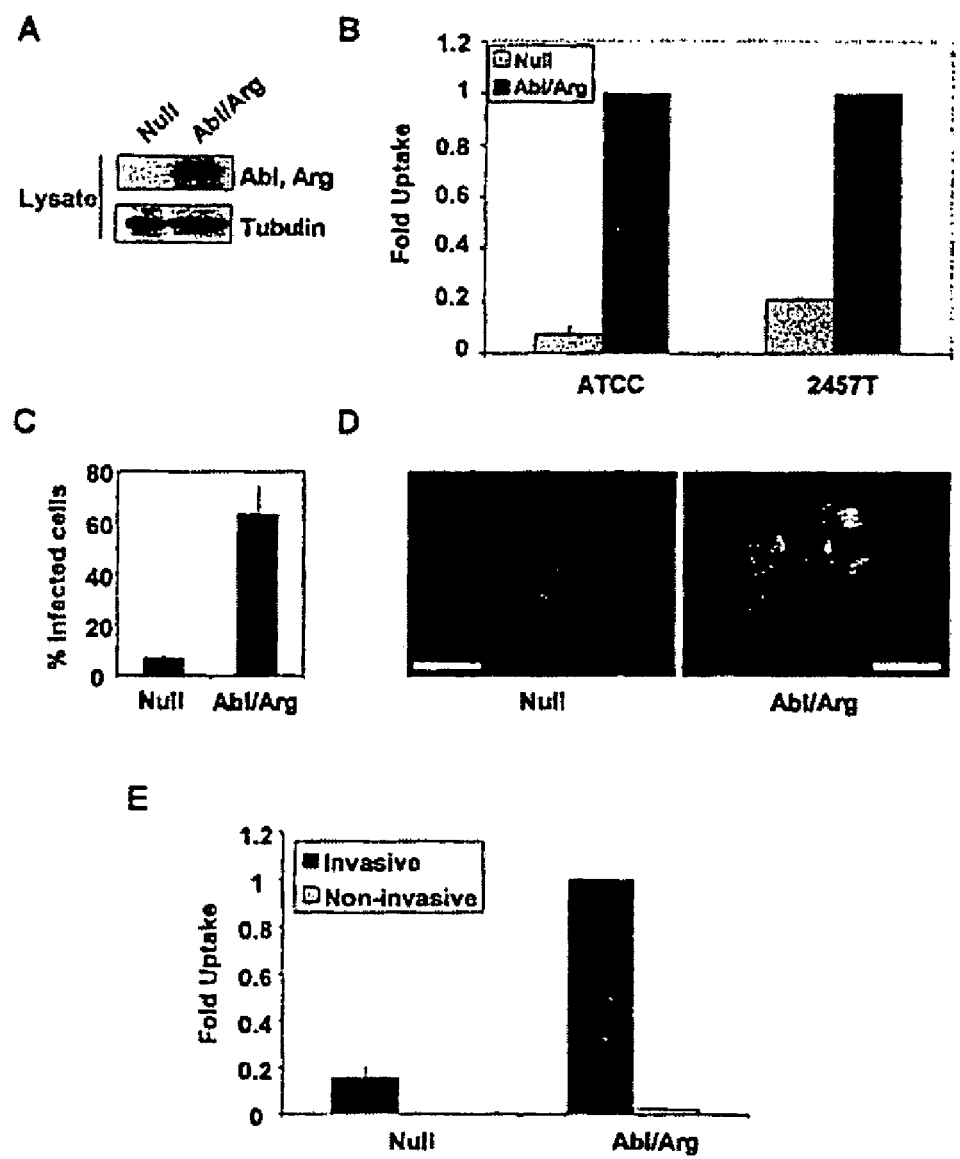
FIGS. 2A-2E. Abl and Arg are required for *Shigella* internalization.
Figure 8:
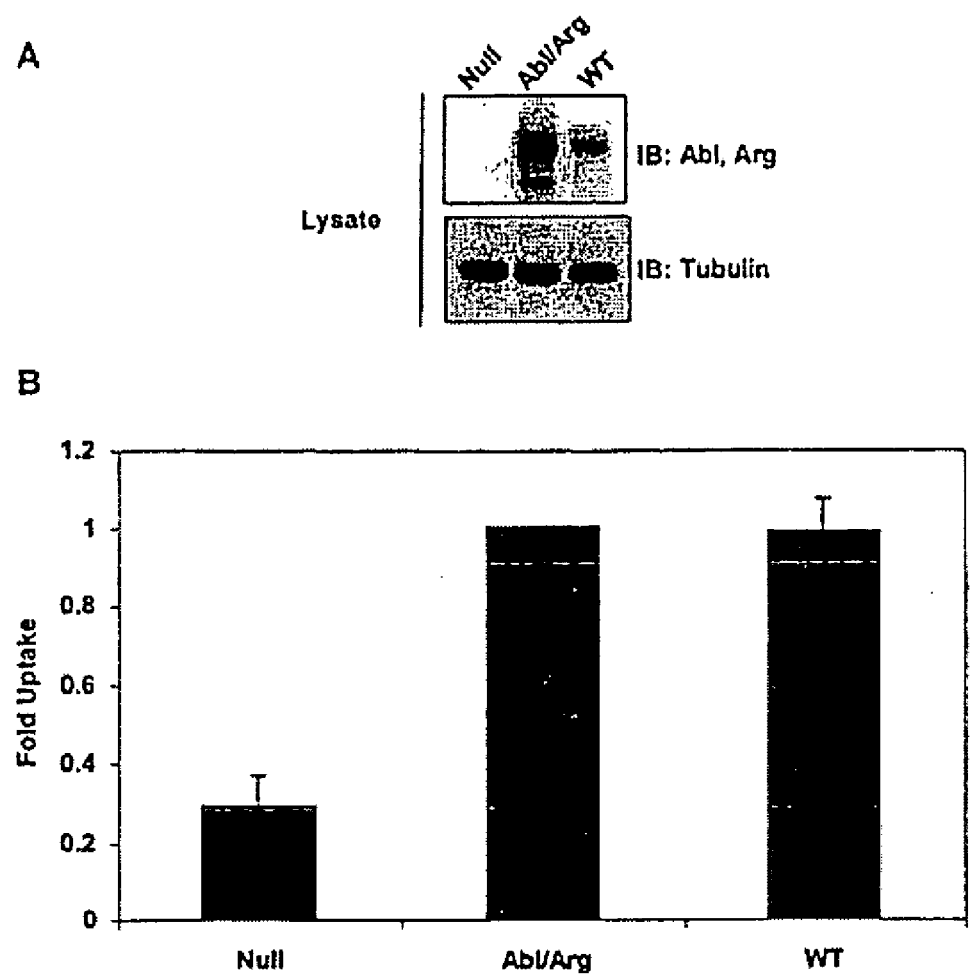
FIGS. 8A and 8B. Shigella is internalized similarly in Abl/Arg-reconstituted MEFs and wild-type MEFs.

To determine whether the Abl kinases are involved in the uptake of *Shigella flexneri*, mouse embryo fibroblasts (MEFs) were employed that lack both Abl and Arg. These cells were reconstituted with either vector alone (Null) or with Abl and Arg (Abl/Arg), to levels similar to those of endogenous Abl and Arg proteins (Plattner et al, Nat. Cell Biol. 5:309-319 (2003)) (FIG. 2A, FIG. 8). The ability of these cell lines to internalize two different strains of *Shigella flexneri* was compared by the gentamicin protection assay (FIG. 2B). A 93% decrease in the number of intracellular bacteria (*S. flexneri* strain ATCC® serotype 2a) was observed in cells lacking Abl and Arg (p value=0.001). The Null cells also exhibited a 79% decrease in uptake using the more invasive *Shigella flexneri* strain 2457T (p value=0.0002). The reconstituted Abl/Arg MEFs internalized *Shigella flexneri* 2457T to the same level as wild-type MEFs (FIG. 8). Bacterial uptake in these cell lines was examined by immunofluorescence microscopy, and the percentage of cells containing intracellular *Shigella* quantitated. The Null cells exhibited a 90% decrease in the number of infected cells, compared to the reconstituted Abl/Arg cells (p value<0.0001) (FIG. 2C). Notably, while most of the Abl/Arg cells engulfed several bacteria, the large majority of Null cells remained uninfected (FIG. 2D). To demonstrate that the bacterial uptake observed in these MEF cell lines was dependent upon the TTSS, the level of uptake of an invasive strain of *Shigella* 2457T was compared to a non-invasive strain that has lost the virulence plasmid (FIG. 9). While the invasive strain readily infected the Abl/Arg-expressing MEFs, the level of uptake of the non-invasive strain was negligible in these cells (FIG. 2E). Additionally, there was no significant difference in the low level of uptake between the Null and Abl/Arg cells using the non-invasive strain (FIG. 2E). These observations demonstrate that Abl and Arg are specifically required for TTSS-mediated internalization of *Shigella*.

Figure 3:
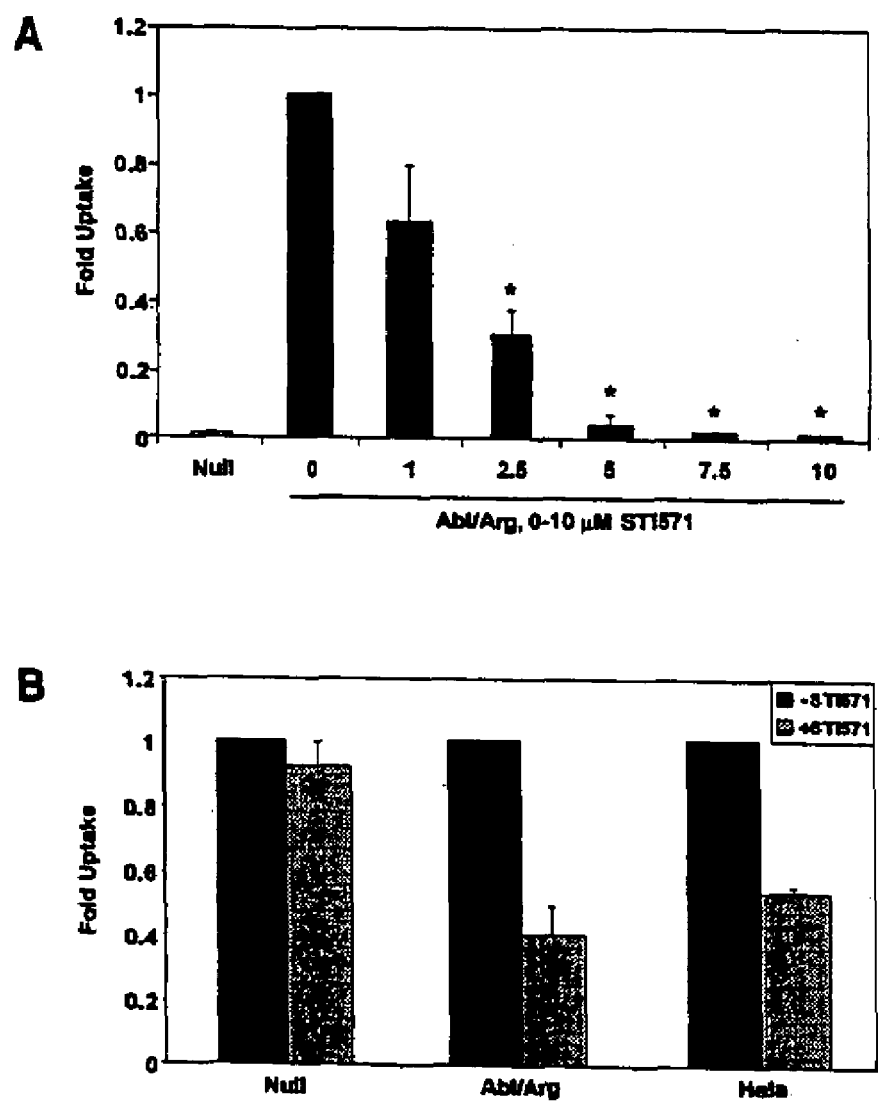
FIGS. 3A and 3B. Abl and Arg kinase activities are required for *Shigella* uptake.

To determine whether the catalytic activities of Abl and Arg are required for bacterial uptake, a specific inhibitor of the Abl family kinases, STI571, also known as Gleevec™ (Druker et al, N. Eng. J. Med. 344:1038-1042 (2001)), was used. This compound does not inhibit other nonreceptor tyrosine kinases, including Src (Buchdunger et al, Eur. J. Cancer 38(Suppl 5):S28-36 (2002), Nagar et al, Cell 112: 859-871 (2003)). Abl/Arg-expressing cells were infected with *Shigella flexneri* ATCC® serotype 2a in the presence of increasing concentrations of STI571. A dose-dependent decrease in the ability of Abl/Arg cells to be infected with *Shigella* was observed (FIG. 3A). At the 5 µM concentration of STI571, the level of *Shigella* uptake was reduced to that of the Null MEFs, and the 10 µM concentration inhibited internalization by 98%, compared to untreated cells (p value<0.0001). The ability of STI571 to inhibit cellular uptake by the more invasive *Shigella flexneri* strain 2457T was also examined. Addition of 10 µM STI571 resulted in a 60% reduction in uptake of *Shigella flexneri* 2457T into Abl/Arg cells (p value=0.0243), and a 47% reduction in Hela cells (p value=0.0018), demonstrating that the observed effect is not cell-type specific (FIG. 3B). Additionally, STI571 treatment had no significant effect on bacterial uptake in the Null cells (FIG. 3B), suggesting that the specific targets of this inhibitor are Abl and Arg. Taken together, these findings show that efficient *Shigella flexneri* uptake requires functional Abl family tyrosine kinases. Abl family kinases are activated during *Shigella* uptake The ability of STI571 to prevent uptake of *Shigella flexneri* suggested that the Abl family tyrosine kinases might become catalytically activated during infection. To test this hypothesis, Abl and Arg kinase activity was examined in cells infected with *Shigella flexneri* from 0-30 minutes, the length of time required for bacterial entry into the cell (Dehio et al, EMBO J. 14:25471-2482 (1995)). Both Abl and Arg were catalytically activated during infection by *Shigella flexneri*, with their activities increasing greater than two-fold over uninfected cells at the 30-minute timepoint (FIG. 4A). Another approach to examine the activation of the Abl family kinases is through analysis of the phosphorylation state of the adapter protein Crk at tyrosine 221. Abl is known to specifically phosphorylate this site on Crk, resulting in a conformational change, thereby altering the ability of Crk to interact with other signaling effectors (Feller et al, EMBO J. 13:2341-2351 (1994)). Crk was immunoprecipitated from lysates of cells at various stages of infection by *Shigella flexneri*, and the immunoprecipitates were analyzed with an antibody that specifically recognizes phosphorylation of Crk at tyrosine 221 (FIG. 4B, upper panels). An increase in tyrosine phosphorylation of Crk at tyrosine 221 was observed, with maximal phosphorylation occurring at the 30-minute timepoint. The Src tyrosine kinase has been previously demonstrated to have a role in *Shigella* uptake (Dumenil et al, J. Cell Biol. 143:1003-1012 (1998)), and has been functionally linked to Abl activation in response to growth factors (Plattner et al, Genes Dev. 13:2400-2411 (1999)). Thus, the activation of endogenous Src during *Shigella* infection was examined by immunoblotting with an antibody that recognizes the activated form of Src (FIG. 4B, lower panels). The activation of endogenous Src followed an equivalent time course as the activation of endogenous Abl and Arg, and Src and the Abl kinases were catalytically activated to a similar extent.

Tyrosine Phosphorylation of Crk is Required for *Shigella* Uptake

Phosphorylation of Crk at tyrosine 221 has been observed following stimulation by growth factors and integrins, and has been shown to regulate the activity of Rac (Abassi and Vuori, EMBO J. 21:4571-4582 (2002)). In these systems, Abl and Arg have been shown to specifically phosphorylate tyrosine 221 on Crk (Kain and Klemke, J. Biol. Chem. 276:16185-16192 (2001)). The observation that Crk becomes tyrosine phosphorylated during *Shigella* infection suggests that Crk may play a role in the signaling pathways mediating bacterial uptake downstream of Abl family kinases. Cortactin has also been previously identified as a target of tyrosine kinases during *Shigella* uptake (Dehio et al, EMBO J. 14:2471-2482 (1995)). A determination was made as to whether phosphorylation of Crk and cortactin was reduced in *Shigella*-infected cells lacking Abl kinase activity, and whether tyrosine phosphorylation of Crk and cortactin during infection was required for the cellular uptake of *Shigella*. To this end, the tyrosine phosphorylation levels of the adapter proteins Crk and cortactin were examined during *Shigella* infection in cells either lacking or re-expressing both Abl and Arg. Crk and cortactin were immunoprecipitated from Null and Abl/Arg cells at various time points during *Shigella* infection, and their tyrosine phosphorylation states were examined by immunoblotting. The phosphorylation of Crk at tyrosine 221 was completely ablated in cells lacking Abl and Arg (FIG. 5, upper panels).

The tyrosine phosphorylation of cortactin was diminished in cells lacking the Abl tyrosine kinases but a minimal level of inducible phosphorylation remained (FIG. 5A, lower panels). A decrease in tyrosine phosphorylation of Crk and cortactin was observed during infection of Hela cells that were pre-treated with STI571 (FIG. 5B). These data demonstrate that Abl and Arg contribute to the regulation of cortactin tyrosine phosphorylation and are required for phosphorylation of Crk tyrosine 221 during *Shigella flexneri* infection, and suggest that Crk phosphorylation plays a role during bacterial uptake. To determine whether phosphorylation of Crk at tyrosine 221 is required during *Shigella* infection, expression of either wild-type chicken Crk (Crk-WT) or a Crk mutant containing a tyrosine to phenylalanine substitution at position 222 (Crk-YF), which corresponds to tyrosine 221 in the human and murine forms of Crk (FIG. 5C), was effected. The effect of expression of these Crk constructs on bacterial internalization was examined using the gentamicin protection assay. Expression of wild-type Crk did not significantly reduce bacterial uptake, compared to the vector control using either strain of *Shigella*. However, expression of Crk-YF resulted in a 65-70% inhibition of bacterial uptake of both *Shigella* strains (FIG. 5D). These data demonstrate that phosphorylation of Crk by the Abl family kinases is an essential step for efficient *Shigella* internalization.

Cdc42 and Rac Activation is Regulated by Abl Kinases During *Shigella* Infection Abl has been previously linked to the Rho family GTPases, through genetic studies in *Drosophila*, and loss-of-function studies in mammalian fibroblasts (Pendergast, Adv. Cancer Res. 85:51-100 (2002), Plattner et al, Nat. Cell Biol. 5:309-319 (2003), Plattner et al, Genes Dev. 13:2400-2411 (1999)). Additionally, phosphorylation of the Abl substrate Crk at tyrosine 221 modulates the ability of Crk to interact with other signaling effectors, and has been shown to regulate the localization of Rac, and Rac-dependent signaling (Abassi and Vuori, EMBO J. 21:4571-4582 (2002)). The observations that Abl-mediated tyrosine phosphorylation of Crk is required for bacterial uptake led to the hypothesis that Abl and Arg might be functionally linked to the activation of the Rho family GTPases during *Shigella* infection. To test this hypothesis, the levels of activated Rac and Cdc42 were examined during *Shigella* infection of cells either lacking or re-expressing Abl and Arg. In Abl/Arg-expressing cells, *Shigella* infection increased Rac and Cdc42 activities, peaking at an average of 3.7-fold and 1.5-fold, respectively, over uninfected cells. In contrast, this increase in Rac and Cdc42 activity was not observed in cells lacking Abl and Arg (FIG. 6A, 6B). These data suggest that the Abl family kinases mediate the activation of the Rho family GTPases during *Shigella* infection. A prediction from this finding is that expression of activated forms of Cdc42 and Rac in cells lacking Abl and Arg would rescue the ability of the Null cells to engulf bacteria. Indeed, a dramatic increase in the ability of the Null cells to internalize *Shigella* in the presence of activated Cdc42 and.Rac was observed (FIG. 6C, 6D). These data demonstrate that activation of the Rho family GTPases can compensate for the loss of Abl and Arg during *Shigella* infection. Since Crk phosphorylation by the Abl family kinases is a major signaling event regulating bacterial uptake (FIG. 5D), a determination was made as to whether the Crk-Y221F mutant had an effect on the activation of Rac and Cdc42 during *Shigella* infection. Indeed, Crk-Y221F expression reduced Cdc42 and Rac activation by 32% and 66%, respectively, while expression of Crk-WT had no significant effect (FIG. 6E, 6F). Taken together, these observations define a signaling pathway activated during *Shigella* infection that connects the Abl family kinases to tyrosine phosphorylation of Crk and to the activation of Rac and Cdc42.

Figure 7:
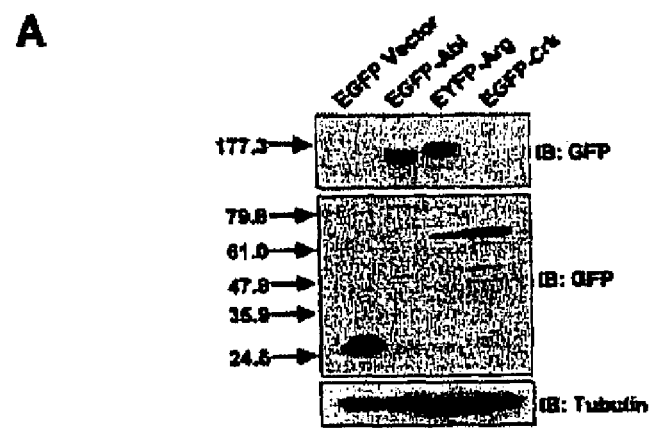
FIGS. 7A and 7B. Abl, Arg, and Crk localize to the site of bacterial entry.
Figure 7:
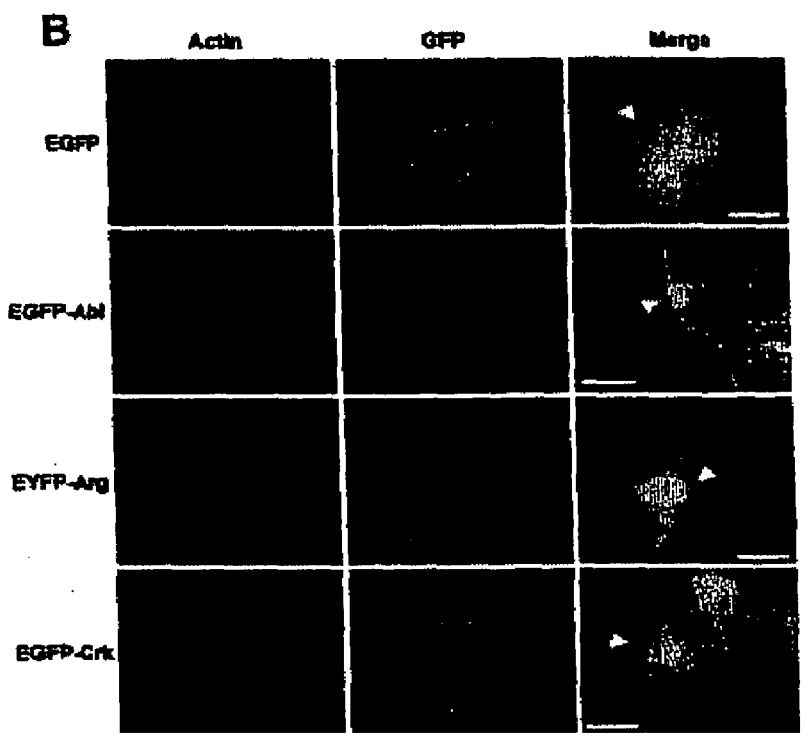

Abl, Arg, and Crk Localize to the Sites of *Shigella* Entry within the Host Cell A novel signaling pathway activated during *Shigella* infection has been identified that involves the Abl family kinases and the adapter protein Crk. To visualize the participation of these signaling molecules in *Shigella* internalization, immunofluorescence microscopy was used to localize Abl, Arg, and Crk to sites of bacterial entry. At the onset of *Shigella* infection, the activation of host cell signaling pathways results in the formation of actin foci at sites of bacterial entry (Adam et al, J. Cell Biol. 129:367-381 (1995)). Co-localization with these large clusters of actin has been used to implicate a number of host cell signaling molecules in *Shigella* uptake, including Src and the Rho family GTPases (Adam et al, EMBO J. 15:3315-3321 (1996), Dehio et al, EMBO J. 14:25471-2482 (1995), Dumenil et al, J. Cell Sci. 113:71-80 (2000), Mounier et al, J. Cell Sci. 112:2069-2080 (1999)). A similar approach was used to localize Abl, Arg, and Crk to sites of bacterial entry, employing fluorescently-tagged versions of these signaling proteins. Hela cells were transfected with EGFP vector, EGFP-Abl, EYFP-Arg, or EGFP-Crk (FIG. 7A), and infected with *Shigella flexneri* 2457T prior to fixation. The cells were immunostained with DAPI to localize the bacteria, Rhodamine-phalloidin to label the actin (FIG. 7B, left panels) and anti-GFP to label the EGFP/EYFP-tagged proteins (FIG. 7B, middle panels). Abl and Arg both localized at the cell periphery, and were concentrated at sites of bacterial entry (FIG. 7B, middle and right panels). Crk localized to the cell periphery in a more punctate pattern, and was also enriched at the actin foci (FIG. 7B, middle and right panels). These patterns of localization were not observed cells expressing GFP alone, demonstrating that the localization of Abl, Arg, and Crk was specific (FIG. 7B, uppermost panels). The findings that the Abl kinases and Crk localize to sites of bacterial entry provide further support for a role of these signaling molecules in *Shigella* internalization.

Conclusions

The studies described above reveal a novel role for the Abl tyrosine kinases in bacterial pathogenesis. They demonstrate a requirement for the Abl family of tyrosine kinases in the cellular uptake of *Shigella flexneri*. Additionally, the Abl kinases are catalytically activated during the initial stages of *Shigella* infection, and mediate the tyrosine phosphorylation of the adapter protein Crk, an event that contributes to efficient *Shigella* uptake. Abl family kinases and Crk accumulate at the site of bacterial entry. A signaling pathway triggered by bacterial infection is defined that leads to the catalytic activation of Abl and Arg tyrosine kinases, phosphorylation of Crk, and activation of the Rho family GTPases Cdc42 and Rac.

Previously, the cytoplasmic pool of Abl and Arg has been implicated in signaling pathways downstream of growth factor receptors, such as PDGF (Plattner et al, Genes Dev. 13:2400-2411 (1999)). The signaling pathways activated during the initial stages of infection by *Shigella flexneri* are strikingly similar to those involved in growth factor receptor signaling. Src is activated by both growth factor stimulation and *Shigella flexneri* infection, as are the Rho family GTPases (Dumenil et al, J. Cell Biol. 143:1003-1012 (1998), Mounier et al, J. Cell Sci. 112:2069-2080 (1999)). In the above study, it is demonstrated that the Abl kinase, another component of the PDGF receptor signaling pathway, is also activated during *Shigella* infection. Following stimulation of the PDGF receptor, Abl activity increases three-fold (Plattner et al, Genes Dev. 13:2400-2411 (1999)), which is similar to the level of activation of both Abl and Arg during *Shigella* infection (FIG. 9A). This increase in Abl kinase activity is likely to reflect the localized activation of Abl kinases at specific subcellular compartments, such as the site of bacterial entry, or at the membrane in growth factor-stimulated cells. Cells lacking Abl exhibit a dramatic reduction in membrane ruffling in response to PDGF, indicating that small changes in overall Abl kinase activity are sufficient to mediate the cellular response to extracellular stimuli (Plattner et al, Genes Dev. 13:2400-2411 (1999)). The above study shows that the induction of Abl and Arg kinase activity is essential for efficient *Shigella* infection, since disruption of these kinases either by targeted deletion or pharmacological inhibition interferes with bacterial uptake. A recent manuscript has provided further support for the requirement of Abl kinase activity during *Shigella* invasion, by reporting that inhibition of PLCγ, a downstream target of the PDG.F receptor, with the PLCγ inhibitor U73122 blocks signaling pathways induced during *Shigella* invasion (Tran Van Nhieu et al, Nature Cell Biology 5:720-726 (2003)). A link between PLCγ and Abl kinase activation was recently identified, and it was demonstrated that the U73122 inhibitor blocks the catalytic activation of Abl following stimulation of the PDGF receptor (Plattner et al, Nat. Cell Biol. 5:309-319 (2003)). These observations further support a link between the Abl family kinases and signaling events that occur during *Shigella* infection.

Figure 6:
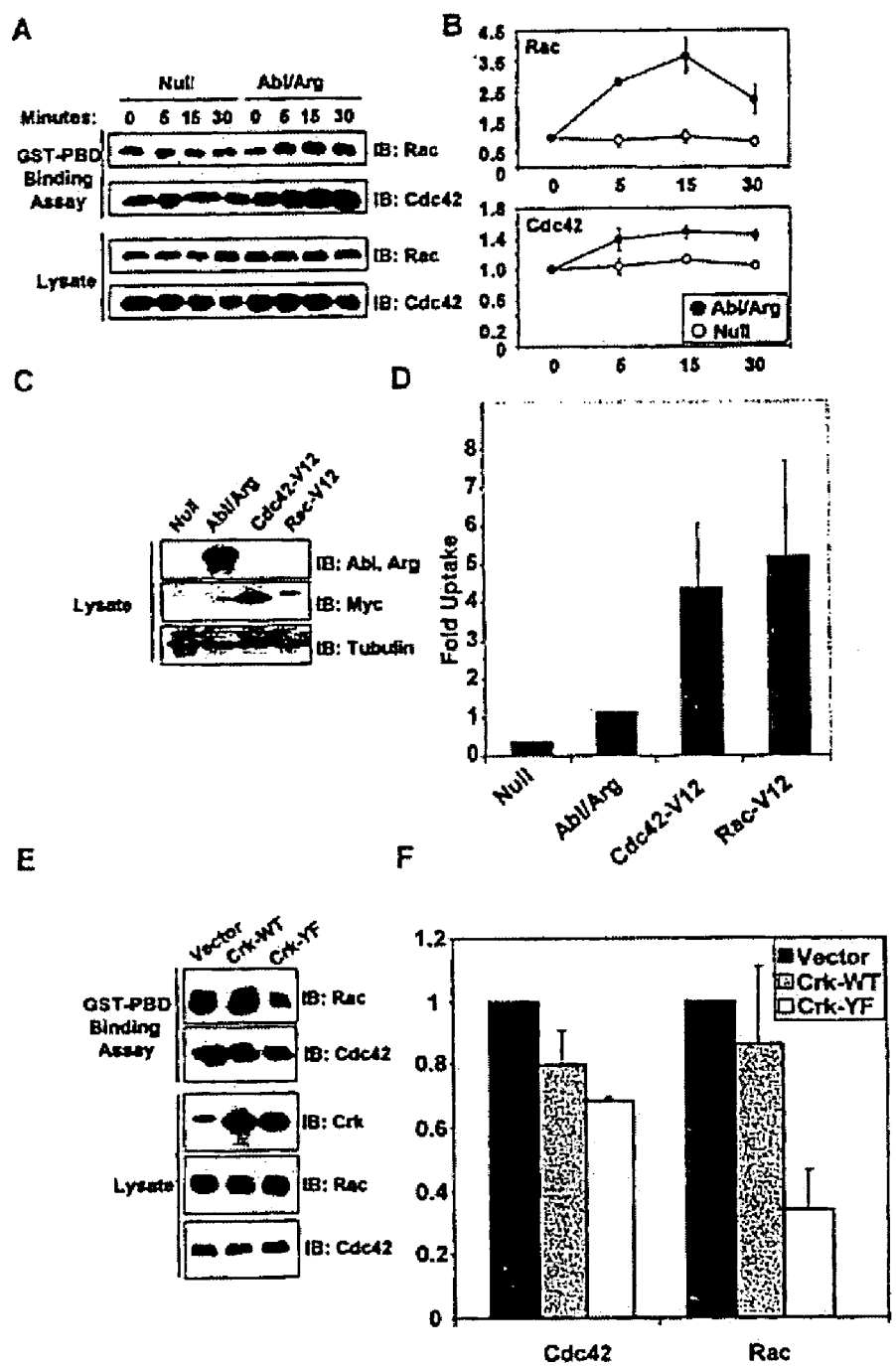
FIGS. 6A-6F. The Abl kinases act upstream of activation of Cdc42 and Rac during *Shigella* infection.

The adapter protein Crk has been identified as a downstream target of Abl and Arg kinase activity during *Shigella* infection. Phosphorylation of Crk at tyrosine 221 by Abl during cell spreading and migration has been well documented (Escalante et al, J. Biol. Chem. 275:24787-24797 (2000), Kain and Klemke, J. Biol. Chem. 276:16185-16192 (2001)). Prior to these findings, Crk had not been identified as a target of tyrosine kinases during *Shigella* infection. The fact that this site remains unphosphorylated in cells lacking the Abl family kinases demonstrates that Crk is a major target of Abl and Arg during *Shigella* infection (FIG. 5A). Additionally, it has been shown that phosphorylation of Crk by Abl kinases promotes *Shigella* internalization, since expression of a Crk mutant that can no longer be phosphorylated by Abl causes a reduction in bacterial uptake. Previous studies have demonstrated that Crk mediates the activation of Rac downstream of growth factors and integrins, and that expression of dominant negative mutants of Crk inhibits Rac-dependent cell processes such as cell migration and lamellipodia formation (Abassi and Vuori, EMBO J. 21:4571-4582 (2002)). A new link between Crk phosphorylation and activation of the Rho GTPases is provided by the showing that the Crk-Y221F mutant inhibits Rac and Cdc42 activation during *Shigella* infection (FIG. 6). The data suggest that Crk is a component of the host cell signaling pathway that mediates bacterial uptake, linking upstream signals from the Abl kinases to GTPases during *Shigella* infection.

Previous studies using genetics and cell biology have suggested links between the Abl kinases and cellular processes regulated by the Rho family GTPases Rac and Cdc42 (Pendergast, Adv. Cancer Res. 85:51-100 (2002), Plattner et al, Nat. Cell Biol. 5:309-319 (2003)), Plattner et al, Genes Dev. 13:2400-2411 (1999)). However, these studies did not show a requirement for the Abl kinases in the activation of Rac and Cdc42 in response to extracellular stimuli. It has now been demonstrated that the Abl family kinases are required for the activation of Rac and Cdc42 during cellular infection by *Shigella flexneri*. Cells lacking Abl and Arg are unable to activate endogenous Rac and Cdc42 in response to *Shigella* infection. In contrast, cells expressing Abl and Arg exhibit a 3.7-fold and 1.5-fold activation of Rac and Cdc42, respectively. These increases are consistent with the 1.7-fold activation of Rac observed following stimulation of the PDGF receptor (Hawkins et al, Curr. Biol. 5:393-403 (1995)). Previous studies have demonstrated a requirement for Rac and Cdc42 during *Shigella* uptake using expression dominant negative mutants, but activation of the endogenous GTPases was not determined (Dumenil et al, J. Cell Sci. 113:71-80 (2000), Mounier et al, J. Cell Sci. 112:2069-2080 (1999)). Measurement of the activation of endogenous Rac and Cdc42 during *Shigella* infection demonstrates that the Abl kinases mediate this response. Furthermore, expression of activated Rac and Cdc42 can rescue the ability of cells lacking Abl and Arg to engulf *Shigella flexneri*. In contrast, expression of these mutants in wild-type cells has no effect on *Shigella* uptake, consistent with previous findings (Mounier et al, J. Cell Sci. 112:2069-2080 (1999)). Expression of the activated GTPases in the Null cells may compensate for the lack of inducible Rac and Cdc42 activity exhibited by cells lacking Abl and Arg (FIG. 6). Together, these observations indicate that Abl and Arg are upstream components in the signaling pathway regulating the activation of Cdc42 and Rac. Indeed, the requirement for Abl and Arg during *Shigella* entry is similar to that of Rac and Cdc42. Expression of dominant negative forms of Rac and Cdc42 in Hela cells reduced the levels of *Shigella* internalization by 68-74% (Mounier et al, J. Cell Sci. 112:2069-2080 (1999)). Similarly, mouse embryo fibroblasts derived from Cdc42 knockout mice exhibit a 68-85% reduction in *Shigella* entry, compared to wild-type fibroblasts (Shibata et al, Curr. Biol. 12:341-345 (2002)). Abl/Arg-null fibroblasts exhibit a 79% to 93% decrease in *Shigella* infection, depending on the strain employed. While the activities of both Rac and Cdc42 have been shown to be required for the uptake of *Shigella flexneri*, the mechanism of their activation has not been fully explored (Mounier et al, J. Cell Sci. 112:2069-2080 (1999)). The data presented above support a model whereby activation of the Rho family GTPases during *Shigella* internalization is preceded by the activation of the Abl family kinases, and the tyrosine phosphorylation of Crk.

The requirement for Abl and Arg during *Shigella flexneri* infection identify these kinases as targets for antimicrobial therapy. Antibiotic resistance to *Shigellae* is widespread, and the development of novel strategies to treat shigellosis is imperative (Sack et al, Clin. Infect. Dis. 24(Supp 1):S102-105 (1997)). The above findings indicate that inhibition of Abl and Arg with STI571 can be used as novel strategy to treat *Shigella* infections. STI571, also known as Gleevec™, was approved by the Federal Drug Administration in 2001, and has been successful in the treatment of Bcr-Abl-positive chronic myelogenous leukemia patients with minimal side effects (Druker et al, N. Eng. J. Med. 344:1038-1042 (2001)). Inhibition of the Abl kinases represents a unique approach to antimicrobial therapy, as it targets host cell proteins, rather than the infectious agent itself.

All documents and other information sources cited above are hereby incorporated in their entirety by reference.

What is claimed is:

1. A method of preventing or treating a pathogen infection, wherein said pathogen is a bacterial or viral pathogen, comprising administering to a mammal in need of such prevention or treatment an inhibitor of Abl tyrosine kinase in an amount sufficient to effect said prevention or treatment.

2. The method according to claim 1 wherein said pathogen is a bacterial pathogen.

3. The method according to claim 2 wherein said bacterial pathogen is selected from the group consisting of *Shigella flexneri*, Enteropathogenic *E. coli* and *Salmonella*.

4. The method according to claim 3 wherein said viral pathogen is vaccinia.

5. The method according to claim 2 wherein the bacterial pathogen is *Shigella*.

6. The method according to claim 1 wherein said pathogen is a viral pathogen.

7. The method according to claim 1 wherein said method is a method of treatment.

8. The method according to claim 1 wherein said method said mammal is a human.

9. The method according to claim 1 wherein said inhibitor inhibits Abl tyrosine kinase indirectly.

10. The method according to claim 1 wherein said pathogen requires Abl tyrosine kinase to infect mammalian cells.

11. The method according to claim 10 wherein said pathogen is a bacterial pathogen.

12. The method according to claim 1 wherein said pathogen catalytically activates Abl tyrosine kinase during infection of mammalian cells.

13. The method according to claim 1 wherein said inhibitor of Abl tyrosine kinase is STI571.

14. The method according to claim 13 wherein said pathogen is a bacterial pathogen.

15. The method according to claim 14 wherein said bacterial pathogen is *Shigella*.

16. A method of preventing or treating a pathogen infection, wherein said pathogen is *Shigella flexneri*, comprising administering to a mammal in need of such prevention or treatment an amount of STI571 sufficient to effect said prevention or treatment.

17. The method according to claim 16 wherein said method is a method of treatment.

18. The method according to claim 16 wherein said mammal is a human.

* * * * *